(12) United States Patent
Larsen (10) Patent No.: US 10,493,718 B2
(45) Date of Patent: Dec. 3, 2019

(54) ABSORBING AIRLAID PRODUCT

(71) Applicant: AIRLAID A/S, Hammel (DK)

(72) Inventor: Jes Kjær Larsen, Beder (DK)

(73) Assignee: AIRLAID A/S, Hammel (DK)

( * ) Notice: Subject to any disclaimer, the term of this patent is extended or adjusted under 35 U.S.C. 154(b) by 864 days.

(21) Appl. No.: 14/784,072

(22) PCT Filed: Apr. 10, 2014

(86) PCT No.: PCT/DK2014/050088
§ 371 (c)(1),
(2) Date: Oct. 13, 2015

(87) PCT Pub. No.: WO2014/166499
PCT Pub. Date: Oct. 16, 2014

(65) Prior Publication Data
US 2016/0052228 A1    Feb. 25, 2016

(30) Foreign Application Priority Data

Apr. 10, 2013   (DK) .................................. 2013 70192
Dec. 23, 2013   (DK) .................................. 2013 70821

(51) Int. Cl.
*B32B 5/02*   (2006.01)
*B32B 7/05*   (2019.01)
(Continued)

(52) U.S. Cl.
CPC ........ *B32B 5/022* (2013.01); *A61F 13/15658* (2013.01); *A61F 13/534* (2013.01);
(Continued)

(58) Field of Classification Search
CPC ....... B32B 38/06; B32B 7/08; B32B 37/0084; D04H 3/08; D04H 3/16; D04H 1/425;
(Continued)

(56) References Cited

U.S. PATENT DOCUMENTS 4,100,324 A * 7/1978 Anderson ............ C11D 17/049
                                              156/167
4,784,892 A * 11/1988 Storey .................... B32B 38/06
                                              15/209.1

(Continued)

FOREIGN PATENT DOCUMENTS

DE    10218259 A1   11/2003
EP    0202472 A1    11/1986
(Continued)

OTHER PUBLICATIONS

Danish Search Report, Application No. PA 2013 70821; 4 pgs.
Danish Search Report, Application No. PA 2013 70192; 1 pgs.

*Primary Examiner* — Betelhem Shewareged
(74) *Attorney, Agent, or Firm* — Schmeiser, Olsen & Watts, LLP (57) ABSTRACT

A liquid-absorbing multi-layered sheet with a liquid-absorbing central layer and a first and a second outer layer of fibers, tissue or film provided at each their side of the central layer is provided. The central layer is airlaid and includes cellulosic fibers, superabsorbents and heat-adhesive binder fibers. The sheet is peculiar in that the percentage of heat-adhesive binder fibers in the central layer is between 1% and 7% of the total weight of fibers in the central layer. In production, a continuous web with the three layers is conveyed through a heating zone for heating the web, wherein the heating temperature and the heating time are adapted to at least a partial melting of the heat-adhesive binder fibers in the central layer for binding the fibers in the central layer and for binding the outer layers to the central layer.

16 Claims, 9 Drawing Sheets

(51) Int. Cl.

| | |
|---|---|
| *A61F 13/15* | (2006.01) |
| *A61F 13/534* | (2006.01) |
| *A61F 13/536* | (2006.01) |
| *B32B 3/30* | (2006.01) |
| *B32B 5/26* | (2006.01) |
| *B32B 27/12* | (2006.01) |
| *B32B 37/06* | (2006.01) |
| *B32B 37/12* | (2006.01) |
| *B32B 37/20* | (2006.01) |
| *B32B 38/06* | (2006.01) |
| *B65D 81/26* | (2006.01) |
| *D04H 13/00* | (2006.01) |
| *B32B 7/08* | (2019.01) |
| *D04H 3/08* | (2006.01) |
| *D04H 1/425* | (2012.01) |
| *B32B 37/00* | (2006.01) |
| *D04H 3/16* | (2006.01) |

(52) U.S. Cl.
CPC .............. *A61F 13/536* (2013.01); *B32B 3/30* (2013.01); *B32B 5/26* (2013.01); *B32B 7/05* (2019.01); *B32B 27/12* (2013.01); *B32B 37/06* (2013.01); *B32B 37/1207* (2013.01); *B32B 37/20* (2013.01); *B32B 38/06* (2013.01); *B65D 81/264* (2013.01); *D04H 13/006* (2013.01); *B32B 7/08* (2013.01); *B32B 37/0084* (2013.01); *B32B 2262/04* (2013.01); *B32B 2307/726* (2013.01); *B32B 2323/043* (2013.01); *B32B 2323/046* (2013.01); *B32B 2553/00* (2013.01); *B32B 2555/02* (2013.01); *D04H 1/425* (2013.01); *D04H 3/08* (2013.01); *D04H 3/16* (2013.01)

(58) Field of Classification Search
CPC ... Y10T 428/24826; Y10T 428/249953; Y10T 428/24322

See application file for complete search history.

(56) References Cited

U.S. PATENT DOCUMENTS

| | | | |
|---|---|---|---|
| 7,195,810 | B1 | 3/2007 | Schmidt et al. |
| 2002/0068081 | A1 | 6/2002 | Fontenot et al. |
| 2002/0169428 | A1 | 11/2002 | Fell et al. |
| 2004/0226834 | A1* | 11/2004 | Baldwin, Jr. ............ B32B 7/08 206/204 |
| 2009/0324893 | A1 | 12/2009 | Soder et al. |
| 2010/0090363 | A1* | 4/2010 | Larsen ................ B29C 47/0021 264/171.23 |
| 2011/0152829 | A1 | 6/2011 | Kawamura |
| 2016/0052228 | A1* | 2/2016 | Larsen ............. A61F 13/15658 604/365 |

FOREIGN PATENT DOCUMENTS

| | | |
|---|---|---|
| EP | 0438113 A1 | 7/1991 |
| EP | 0743995 A1 | 11/1996 |
| WO | WO0166345 A1 | 9/2001 |

\* cited by examiner

Fig. 12

ABSORBING AIRLAID PRODUCT

CROSS-REFERENCE TO RELATED APPLICATIONS

This application claims priority to PCT Application No. PCT/DK2014/050088 having a filing date of Apr. 10, 2014, based on DK PA 2013 70192 having a filing date of Apr. 10, 2013 and DK PA 2013 70821, having a filing date of Dec. 23, 2013, the entire contents of which are hereby incorporated by reference.

FIELD OF TECHNOLOGY

The following concerns an absorbing product of airlaid material and a method for production thereof. The following particularly concerns a product including a liquid-absorbing multi-layered sheet with a liquid-absorbing central layer and a first and a second outer layer of fibres, tissue or film provided at each their side of the central layer; wherein the central layer is airlaid and includes cellulosic fibres, superabsorbents and heat-adhesive binder fibres; wherein the percentage of heat-adhesive binder fibres in the central layer is between 1% and 7% of the total weight of fibres in the central layer. The central layer is an airlaid material and may include cellulosic fibres, superabsorbents (like fibres or granules) and binder fibres (preferably so-called bi-component fibres).

By the production method is produced a continuous airlaid central web of a mixture of cellulosic fibres, superabsorbents and heat-adhesive fibres, where in the central layer there is added heat-adhesive binder fibres which constitute between 1% and 7% of the total weight of the fibres in the central layer; wherein at each their side of the central layer there are provided a first and second continuous outer web of fibres, film or tissue in order to form a 3-layered structure of the web. There is provided a continuous web with three layers which are subsequently calendared.

BACKGROUND

In EP 0 743 995 are disclosed various production methods for a dry-formed airlaid material based on dry-laid cellulosic fibres with a suitable binding, e.g. gluing with latex or by means of binder fibres. The laying of the fibres for the formation of a continuous web is usually effected by defibering and introducing cellulosic material in an airstream that conveys the loose fibres to a former head above a running perforated formerwire, under which is located a suction box for sucking the fibres down against the wire where they are continuously deposited as a coherent gauze with a desired web thickness. Such products are also termed airlaid non-woven. The products are typically utilised as liquid-absorbing sheets, e.g. by incorporating superabsorbing fibres/granulate. In case that binder fibres are used for stabilising the material, the laid airlaid material can be fixed by passing it through a heating zone. Therefore, thin as well as thick webs can be made as the binder fibres will be equally present in outer as well as inner parts of the material web. As mentioned in EP 0 743 995, the admixing percentage of heat adhesive fibres is limited, typically to about 15%, for economic reasons. Referring to EP 0 202 472 in which is described various airlaid products with bi-component binder fibres, the percentage of which being 15% or 25%, it is proposed as an improvement in EP 0 743 995 in order to reduce the percentage of binder fibres to add a surface impregnation with a layer of glue as this glue fixes the lesser fibres which are not held together by the binder fibres, whereby dust raising from the web is prevented as well.

An airlaid multi-layered product, primarily for wet tissues, with a greater percentage of binder fibres is known from International application WO 01/66345. This document discloses an airlaid fibre web with an inner cellulosic layer between two outer layers. For making the outer layer there is used between 50 and 100% binder fibres and between 0 and 60% cellulosic fibres, and for the inner layer is used between 15% and 40% binder fibres and 50% to 90% cellulosic fibres. In preferred embodiments, no other adhesive is applied whereby the web is only held together by binder fibres, e.g. multi-component fibres or bi-component fibres. A structuring treatment by means of rollers is also mentioned as steps in the production.

An example of making an absorbing multi-layered web without binder is mentioned in EP 2 123 440. Herein is disclosed a cellulosic web as a liquid-absorbing central layer between two outer layers that consist of fibres with a fibre diameter between 50 nm and 25 nm. It is only mentioned as a possibility that in the outer layer there may be provided a polymer with low melting point, preferably between 60 and 130°, in order to adhere to the central layer.

As it appears from the above, various techniques have been developed through the years in order to produce stability in absorbing cellulosic materials. Usually, it is so that a high percentage of binder fibres as in WO 01/66345 provide good stability of the product, though causing high costs and limitations in liquid-absorbing capability, therefore often unwanted, why in EP 0 743 995 there is proposed a lesser percentage of binder fibres supplemented with an outer glue layer, and in EP 2 123 440 it is suggested to completely avoid binder fibres and glue.

The fibre web disclosed in EP 2123440 seems at first to be a good solution, particularly because the relatively expensive synthetic binder fibres are saved, and possible superabsorbing fibres can be utilised to a high degree as they can freely expand during absorption of liquid as opposed to a product with a high percentage of binder fibres, where the latter due to their network reduce utilisation of the superabsorbing fibres because of their reduced expansion possibility. However, it has appeared that a product such as in EP 2123440 tend to fall apart if exposed to larger amounts of liquid; in particular it has appeared that it would be desirable with a better stability of the product if used for collecting liquid in trays for e.g. meat, poultry, fish or similar products, where an aesthetic appearance is crucial and where direct contact between the superabsorbing fibres from the central layer and the meat is ideally to be avoided.

In US 2002/0068081 is described a product and a production method as indicated in the introduction. A very airy airlaid fibre web is produced in this system. No compacting of the fibre web is performed after the formerhead as the web is desired to be maintained as airy as possible at the subsequent heating and the following moisturising. After heating the web is supercalendared to a density of at least 500 kg/m$^3$. The calendaring occurs in a cold calendar unit and the web is cooled before calendaring. Smooth calendar rollers are used, imparting the product a smooth surface without embossings in the surface. Since cold calendaring is applied, it is not possible to press the binder fibres into each other during the calendaring. Supercalendaring of the entire surface of the product have several drawbacks. It requires very high pressure and is therefore energy-consuming. Moreover, great demands are put on dimensioning the facility in order to operate with very large pressures. The pressure strains the facility.

By calendaring, hydrogen bonds are formed between cellulosic fibres in the pulp material. Hydrogen bonds are subsequently broken when a product comes into contact with polar fluids (for example aqueous solutions, body fluids, meat juice and the like). When hydrogen bonds are broken, the product will, as opposed to the above-mentioned product according to EP 2 123 440, still have integrity and not fall apart as the binder fibres are bonded to each other and to some of the cellulosic fibres.

Since cold calendaring is used, a bonding of the outer layer cannot be achieved in this product by means of the binder fibres. Therefore there is a need for a separate fastening technique, e.g. gluing, for fastening the outer layers to the central layer.

By this product is intended a certain drape stiffness. Such stiffness is, however, not required for absorbing products which are intended for placing on a support which is the case when used for collecting liquid in trays from e.g. meat, poultry, fish or similar products, or when used in hygienic products.

The ability of the product to expand caused by liquid absorption depends on the distribution of the binder fibres in the product. The mutual attachment of the binder fibres can thus be limiting to the expansion capability of the product and thereby also a limitation to the amount of liquid that may be absorbed.

SUMMARY

An aspect relates to an improved product in the technical area in question. In particular it is an aspect to provide an absorbing fibre product with enhanced stability after absorption of liquid but with the possibility of expansion during liquid absorption. It is also an aspect to minimise the use of binders.

This aspect is achieved by a product as mentioned in the introduction and which is peculiar in that the central layer has a density less than 400 kg/m$^3$, that the multi-layered sheet has embossings that form separate areas which are compressed for establishing attachment points constituting between 10% and 20% of the area of the sheet, preferably about 15%, and that the percentage of the heat-adhesive fibres is preferably between 1% and 5%, more preferred between 2% and 4%. The product is described in detail below.

The production method according to embodiments of the invention is characterised by steps wherein the central web is made with a density which is less than 400 kg/m$^3$; wherein the heat-adhesive binder fibres are preferably added in a percentage between 1% and 5%, preferably between 2% and 4%, wherein the central layer is subjected to a compacting with heated compacting rollers; wherein the web or webs that are made air-permeable are moved through a heating zone for heating the web or webs, respectively, wherein the heating temperature and the heating time is adapted to at least a partial melting of the heat-adhesive binder fibres in the central web in order to bind the fibres in the central web; wherein the formed webs are moistened after the heating zone; wherein webs that possibly are not air-permeable are unwound between the heating zone and a calendar unit which is operated with heated calendar rollers for hot calendaring, whereby the binder fibres are pressed into each other simultaneously with establishing hydrogen bindings between the cellulosic fibres; wherein the central web is always subjected to heating prior to calendaring the jointed webs in the calendar unit, and wherein calendaring performs a patterned embossing with patterned rollers for embossing the surface of the multi-layered web with separate areas which are compressed for establishing attachment points that constitute between 10% and 20% of the area of the web, preferably about 15%.

The product includes a liquid-absorbing multi-layered product with a liquid-absorbing central layer and a first and a second outer layer of fibres, tissue or film provided at each their side of the central layer. The central layer is an airlaid material and includes cellulosic fibres, superabsorbents and heat-adhesive binder fibres, typically in the form of bi-component fibres. Alternatively, mono-component fibres can be used as well.

The airlaid material is peculiar in that the percentage of binder fibres in the central layer is between 1% and 7% of the total weight of fibres in the central layer, e.g. between 1% and 5% or between 2% and 3%. All percentages are percentages of dry weight. In practice it has appeared that a particularly good absorbing capability is achieved by weight percentages between 2% and 3% when between 10% and 20% of the area of the sheet stick together. Surprisingly, it appears hereby that the hydrogen bonds in the attachment points are broken such that the product is easily expanded and can absorb liquid. The binder fibres still retain the integrity of the product as they bind to each other and to the outer layers and to the cellulosic fibres. It can be said that space is created for expansion and for efficient utilisation of the superabsorbents.

It appears that in these products no breaking of the attachment points occurs if more than 7% binder fibres are used. The bonds established by the binder fibres become too strong such that even the hydrogen bonds are broken, the binder fibres will still retain the shape of the product without enabling expansion.

It has appeared as well that products containing less than 1% binder fibres do not have sufficient integrity and that they fall apart by liquid absorption and expansion.

The central layer of the multi-layered sheet has a density which is less than 400 kg/m$^3$.

The embossings form separate areas that are compressed for establishing attachment points. Due to local supercalendaring, a large percentage of hydrogen bonds are produced herein. The limited percentage of the total area of these attachment points cause that there is only need for a supercalendaring in this percentage of the entire area. The previously mentioned drawbacks of supercalendaring are thereby reduced. At the same there are achieved advantages by the hydrogen bonds that contribute to the integrity of the product in dry condition, enabling expansion by absorption, after which the binder fibres alone can ensure integrity of the product.

Use of hot calendaring ensures establishment of bonds between the binder fibres and the outer layers. Hereby separate methods for bonding the outer layers and the central layer are avoided. Integrity in wet and dry condition is thus achieved at least in the area constituted by the attachment points.

It has appeared that a durable and stable product can be provided compared with the prior art with a very small percentage of binder fibres in the central layer, in particular a significant lesser percentage of binder fibres than in standard products with binder fibres. In this way, on the one hand the advantage of reduced costs due to the reduced number of binder fibres is provided for and on the other hand a sufficient stability of the product is provided for such that it retains its integrity even when absorbing relatively large amounts of liquid in the central layer. In addition, the small percentage of binder fibres means that expansion of possible superabsorbing materials (superabsorbents) is not limited to any appreciable degree, increasing the liquid absorbing capability. In a product which has absorbed liquids it will appear that the material in the central layer is far more stable and is less loosened from the outer layers as the binder fibres establish a bond during their activation in a hot calendaring.

There is no need for a product with great density as during the making there is used binder fibres and compacting with heated compacting rollers. The material is compacted between the compacting rollers such that the binder fibres come closer to each other, thereby providing more bonding points which are activated by the subsequent heating. By using heated compacting rollers the fibre web is stabilised before being transferred from the formerwire to the subsequent heating zone.

In practice, it has appeared that the tensile strength is substantially increased after activation in the oven when using compacting rollers.

There is a need for an amount of fibres for meeting requirements for absorption capability. It is possible to absorb large amounts of liquid as between the attachment points there are superabsorbents and cellulosic material which remains relatively airy and thus can contain large amounts of liquid. Since high density and cohesion is only established in the separated attachment points, it will be possible that these attachment points are broken by the absorption, allowing expansion of the product concurrently with absorption of liquid. An increased absorption capability is thus achieved concurrently with the breaking up. The integrity of the product is still ensured by the small amount of binder fibres which in addition to bonding in the central layer also produce adherence between the central layer and the outer layers.

For example, the area of each of the attachment points can be between 1.2 and 2.5 mm$^2$, preferably about 1.7 mm$^2$ The attachment points can be rectangular, preferably square. Alternatively they may have other polygonal shapes or be round or oval.

The bonding force in the product is established by a combination of the bonds of the binder fibres and hydrogen bonds in the cellulosic material. The fibre web is moisturised before calendaring. By varying the degree of moistening there may be achieved control of the amount of hydrogen bonds in the cellulosic material formed during the calendaring. Establishment of hydrogen bonds in products contributes to reducing the need for binder fibres.

By the calendaring there is operated with a linear pressure varying due to the pattern in the calendar rollers. A limited linear pressure is applied compared with calendaring according to prior art wherein there is a uniformly high linear pressure along the entire length of the calendar rollers, operating with supercalendaring and a linear pressure of 143-715 kg/cm. According to embodiments of the present invention, there is no need for supercalendaring. A reduced linear pressure will at the same time reduce the risk of reducing absorption capability as the product becomes less compact and thereby absorbs liquid more easily.

The central layer is a single layer produced separately of fibres, typically as a fibre web, before joining with one or more separately produced layers of fibres. Alternatively, the central layer is formed directly on a previously formed layer and/or web constituting one of the outer layers. A central layer typically has an even and relatively homogenous distribution of fibres through the layer. If several types of fibres are used in a layer, all these types of fibres are typically evenly and homogenously distributed throughout the layer. A layer thereby differs from a multi-layered product where there is not an even and homogenous distribution throughout the entire multi-layered product, precisely because there are several, different layers The multi-layered product can be made with a first outer layer of a film or with both outer layers of film. Alternatively, the outer layers can be tissue or non-woven or a combination of film, tissue or non-woven.

Heat-adhesive binder fibres (typically bi-component fibres) are polymer fibres which by melting or partial melting connect the surrounding fibres. In this way is achieved a so-called heat bonding. The binder fibres are e.g. bi-component fibres with a core and an outer layer where the outer layer has a lower melting temperature than the core. Typically, binder fibres or parts of binder fibres have a low melting point of 80-200° C., preferably 120-170° C., more preferred 130-150° C., and most preferred 135-145° C.

All together there is hereby achieved a product which is particularly suitable for use in hygienic products such as sanitary towels and which is also suitable for collecting liquid from foodstuffs, e.g. juice from meat, poultry, fish or other foodstuffs that give off juice and liquids. However, the product is not limited to these applications and can generally be used for liquid collection.

Producing a product as described will typically occur in long webs in a continuous process. The following production method in detail is applicable. There is produced a continuous airlaid central web of a mixture of cellulosic fibres, superabsorbents and heat-adhesive binder fibres, for example in an airlaid process. A first and a second continuous outer web of fibres, tissue or non-woven or film are supplied from each side of the central web in order thereby to form a multi-layered web with at least three layers, as in principle it is possible to supply further layers.

The web with the at least three layers is then conveyed through a heating zone. For example, such a heating zone is provided as oven where heat supply to the web is effected by radiant heat and heat transmission by air flow through the product, the latter being in contrast to heating with a heated calendar roller where heating occurs by contact heat transmission between the calendar roller and the web. The heating temperature and the heating time are adapted for at least a partial melting of the heat-adhesive binder fibres in the central layer in order to bind the fibres in the central layer and for binding the outer layers to the central layer. In technical terms, this process is termed an activation process of the binder fibres.

After passing through the oven, the product will be very dry, so-called bone dry. Therefore it is moisturised such that hydrogen bonds are enabled in the cellulosic material.

The web is then subjected to a calendaring wherein the central layer and the outer layers are passed through the nip of the calendar rollers and thereby compressed in order for the binder fibres to bond the outer layers to the central layer while at the same time hydrogen bonds are established in the cellulosic material. Moreover, the binder fibres also bond the binder fibres together in the central layer and bond the superabsorbents to the fibres as well. The calendar rollers typically have a temperature between 80° C. and 170° C., preferably about 110° C. The temperature will primarily be based on the speeds applied. Typically, operation is performed at speeds between 20 m/min and 320 m/min, preferably between 120 m/min and 180 m/min. This provides possibility of ensuring activation of the binder fibres and the pressing of them into each other.

For example, first or second or both first and second outer layers are not passed through a heating zone or oven if the "layer" is not air-permeable—in this case the first or second or both first and second outer layers are unwound after the oven and immediately before the calendaring.

The calendaring is performed with a calendar roller which on its surface is provided with local elevations in order thereby to form an embossing pattern for embossing the surface of the web with separated areas that are compressed thereby. Such a calendar roller is provided with an embossing pattern such that only small separated areas of the sheet are compressed, e.g. in punctiform areas or linear areas. This means that intermediate areas between the compressed areas, by adding a small amount of liquid at first, allows a greater absorption/expansion of the material than by the compressions. The content of heat-adhesive binder fibres in the material are adapted together with the thickness and area of the compressions such that the strength in the compressed points is less than the strength of the expansion from the absorbents when the latter absorb the most by further addition of liquid. Maximum utilisation of all absorbents is thereby achieved, and at the same time is achieved a good dimensional stability in the product by means of the heat-adhesive binder fibres.

It is preferred to perform calendaring with two interacting calendar rollers, each provided with an embossing pattern, in order thereby to provide embossing on both sides of the web. The product hereby appears symmetrically. Hereby can be formed a product wherein the sheet has embossings in the form of distinct local depressions applied on either side of the sheet.

For example, the calendaring rollers can be provided on their surface with linear elevations in order thereby to form an embossing pattern in the surface of the multi-layered web.

It is preferred that the linear elevations are formed on both calendar rollers extending at 45° relative to the axial extension of the rollers, wherein the orientation is oppositely directed such that the attachment points are formed where the linear elevations intersect each other. This provides a particularly simple construction which is very robust in use.

It is also possible to perform such an embossing with only one embossing roller from one side of the web which interacts with a plane roller at the opposite side. The sheet is hereby imparted embossings in the form of local, separated depressions as well. These depressions will be most distinct at the side of the sheet in contact with the embossing roller, e.g. where the first outer layer is provided. However, "embossing" will also appear at the opposite side of the product relative to the embossing roller as by embossing there will occur "attachment" of the outer layers such that the layer opposite the embossing roller is "pulled up" by the embossing of the outer layer at the side where the embossing roller acts on the product.

The advantage of a calendaring with an embossing—whether a double-sided embossing or a one-sided embossing—is the possibility of making products that are dimensionally stable and which can be made in a technically simple way at particularly high speeds, e.g. with a speed of the web between 150 m/min and 320 m/min. In order for the calendaring process to run in a satisfactory way cf. the above, it is of utmost importance that a spacing fitting the speed is present between the embossing roller and the opposing smooth calendar roller, and that the surface temperature on both calendar rollers is carefully adapted to the material of first and second outer layers. As mentioned, the surface temperature of the rollers is typically at least 110° C., but may be up to 170° C. However, the temperature depends on the type of film—when using film in the outer layers—and the speed as higher temperatures than melting temperature for the material in the outer layers can be used if operating at very high speeds.

The calendar rollers are heated in order to support the melting process. A combination of activating binder fibres by moving the web through a heating zone, such as an oven, and then through a further heating unit with one or more heated calendar rollers provide a further degree of freedom in controlling the bonding process.

The central layer is advantageously made by airlaid technique and contains hydrophilic cellulosic fibres for absorbing liquid. In order to increase liquid absorption capability, the central layer can be supplemented with superabsorbing materials (superabsorbents), e.g. in the form of superabsorbing fibres (SAF). Alternatively, the superabsorbing material can be in the form of granulate (SAP). However, this will typically be used in a product which is closed along the side edges. Products for less liquid absorption contain alternatively no superabsorbents but only cellulosic and heat-adhesive binder fibres.

For example, the first and second outer layers can be constituted by non-woven layers or tissue. Alternatively, the first outer layer can be constituted by a non-woven layer or tissue and the second outer layer by a film. Such designs are particularly suited for sanitary towels.

For example, the first outer web or both outer webs are made a polymer films such that the first outer layer of the final sheet is constituted by a film, or both outer layers are constituted by film. When using the sheet for collecting liquid from foodstuffs, e.g. meat, it is not desirable that fibres from the sheet adhere to the meat. In order that such film adhere effectively to the binder fibres, the film is advantageously co-extruded polymer film where HDPE (High Density Poly Ethylene) constitutes one side of the polymer film and LDPE (Low Density Poly Ethylene) constitutes the other side of the polymer film, with LDPE facing the central layer. LDPE typically has a lower melting temperature than HDPE, why by this combination there is achieved a suitable strength of the film due to HDPE and an ample adherence of binder fibres to LDPE during the heat treatment. Alternatively, a cheaper homogenous film of LDPE or PP can be used. Alternatively, a film of PES (polyester) or PLA can be used.

Alternatively, the first outer web or both outer webs can be laminated to the central layer by means of direct extrusion with an HDPE, LDPE, PP, PLA layer, or similar materials. Such extrusion occurs immediately before calendaring.

In some embodiments it is important that the sheet along the side edges has a liquid-permeable structure through which liquid can be transported from the edge into the central layer. Cellulosic fibres and binder fibres are effective in transporting liquid in under the film or in between the films as these fibres enhance the capillary action into the central layer. The product can thus be made as a single construction wherein the three layers are formed as webs that are superposed and cut up, without closure along the side edges occurring.

A tight surface is advantageously usable for foodstuff products as the risk of fibres adhering to the foodstuff surface is avoided. In multi-layered sheets for foodstuff products openings in the surface through which fibres from the central layer can penetrate are unwanted. By "tight" surface is thus meant a surface through which fibres from the central layer cannot penetrate. The surface may thus have microscopic apertures. The first outer layer with a tight film is then oriented towards the foodstuff. The liquid from the meat will then run along the surface of the film or to a lesser extent through microscopic apertures in the film and down along the side of the sheet where it is sucked into the central layer.

If a smooth surface is desired towards the meat or other foodstuffs and seepage to the central layer not only from the edge area of the sheet, the lower film can be liquid-permeable such that liquid running down from the upper liquid-impermeable film can penetrate into the central layer from the outer layer at the bottom of the structure. Alternatively, the first outer layer can be perforated. For example, one of the two outer webs or both outer webs can be perforated during the production process before joining with the central layer. No perforation of the calendar roller is then performed. Alternatively, the calendar roller can be designed such that perforation of the outer layer is performed, for example the polymer film, during the calendaring.

Materials for film in the outer layer are e.g. PP (polypropylene), PE (polyethylene), PET (polytetrafluoroethylene), PES (polyester), PA (polyamide), PLA (polylactic acid) and/or silicon polymer. Mixtures thereof can be used as well. Such film can be transparent or coloured, e.g. white, black or blue. The films can be water-impermeable or perforated. A typical thickness applied on the film is 5-40 µm.

Alternatively, one outer layer or both outer layers can be made by means of fibres, particularly non-woven layers, e.g. of the type carded non-woven, spunbond or meltblown, or a combination of these technologies. Typical weight is 5-15 $g/m^2$. Alternatively, an outer layer or both outer layers can be tissue made of cellulose in a wet process. Typical weight is 12-25 $g/m^2$. This is the case typically when the sheet is used in hygienic products.

As a further alternative, one or both outer layers can be made as a thin layer with a predominant weight percentage of bi-component fibres or exclusively bi-component fibres. Such a layer is then 20 $g/m^2$ or 5-15 $g/m^2$, for example 10 $g/m^2$. In the central layer are typically used cellulosic fibres of the type fluff pulp of fully-treated, semi-treated or untreated grades.

As binder fibres is typically used bi-component fibres, e.g. of the polymer combinations PE/PP, PE/PET, PET/coPET, where coPET stands for polytetrafluoroethylene copolymer. Binder fibres made of PLA can form a part as well. The fibre density is advantageously at least 0.8 dtex, e.g. 1.0 dtex. Examples of fibre lengths are 3-12 mm, e.g. 6 mm.

Nanofibres can also be used, e.g. made of polymers PET, PE, PP or PLA.

If binder fibres are used together with other thermoplastic fibres, and when it is not intended that these other thermoplastic fibres can melt, their melting point should lie substantially higher than the melting point of the binder fibres, e.g. 30° higher. The temperature during the heating can then be chosen to melt the binder fibres only.

The thickness of the central layer is typically 0.6-20 mm whereas the outer layers have a much lesser thickness, e.g. 0.02-0.4 mm. The thickness of the central layer is typically 0.8-4 mm after calendaring. The weight of the central layer is typically 50 to 350 $g/m^2$, depending on the desired absorption. A large percentage of the central layer can be superabsorbents in the form of fibres or granulate.

In case that an outer layer or both outer layers are made of fibres and are not to be water-permeable, a lacquer can be applied which stop penetration of liquid.

BRIEF DESCRIPTION

Some of the embodiments will be described in detail, with reference to the following figures, wherein like designations denote like members, wherein.

DETAILED DESCRIPTION

Identical elements appearing in several Figures will not be explained in detail in connection with each figure.

Figure 1:
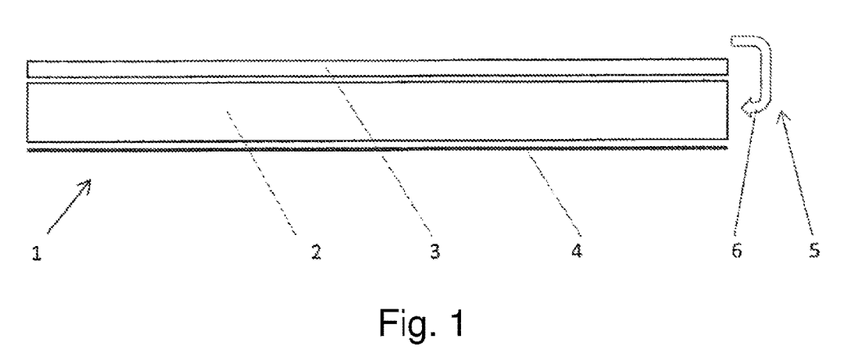
FIG. 1 shows a sheet with a liquid-impermeable film at the top side.

FIG. 1 shows a first embodiment of a sheet 1 with a central layer 2 and a first outer layer 3 provided at one side of the central layer 2, and a second outer layer 4 at the opposite side of the central layer 2. For example, the first outer layer which is oriented upwards on the drawing is a film 3 that prevents seeping of liquid to the central layer 2. The liquid will then flow out to the edge 5 of the sheet and then seep into the central layer from the edge of the sheet 1, as shown by arrow 6. Alternatively or in addition the liquid can gather under the sheet 1 and seep in through the outer layer 4 at the bottom if this is liquid-permeable.

Figure 2:
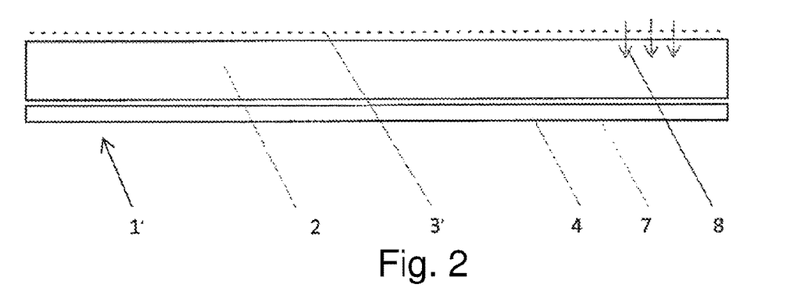
FIG. 2 shows a sheet with a perforated film at the top side.

FIG. 2 shows a second embodiment of a sheet 1' with an upper outer layer 3' which is perforated such that liquid can seep down into the central layer 2 through perforations 7 as shown by the arrows 8.

Figure 3:
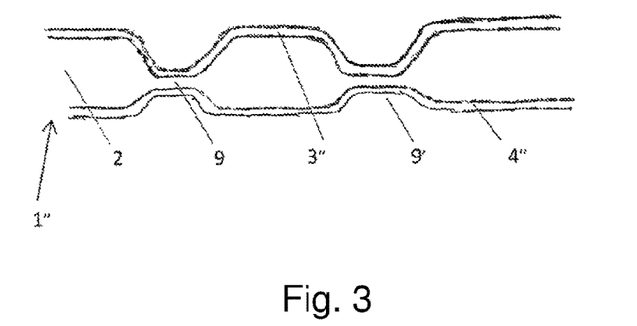
FIG. 3 shows a sheet with three layers and embossing from one side only.

FIG. 3 shows a third embodiment wherein the sheet 1" is compressed in separately embossed areas 9 by patterned embossing with a calendar roller during a production process of the product. These embossed areas 9 constitute the attachment points of the sheet. The embossing with punctiform depressions 9 is only provided from the first outer layer 3" at one side of the sheet 1". A less distinct depression 9' appears in the finished product, produced by the second outer layer 4" being pulled towards the first outer layer 3" at the embossing.

Figures 4, 5:
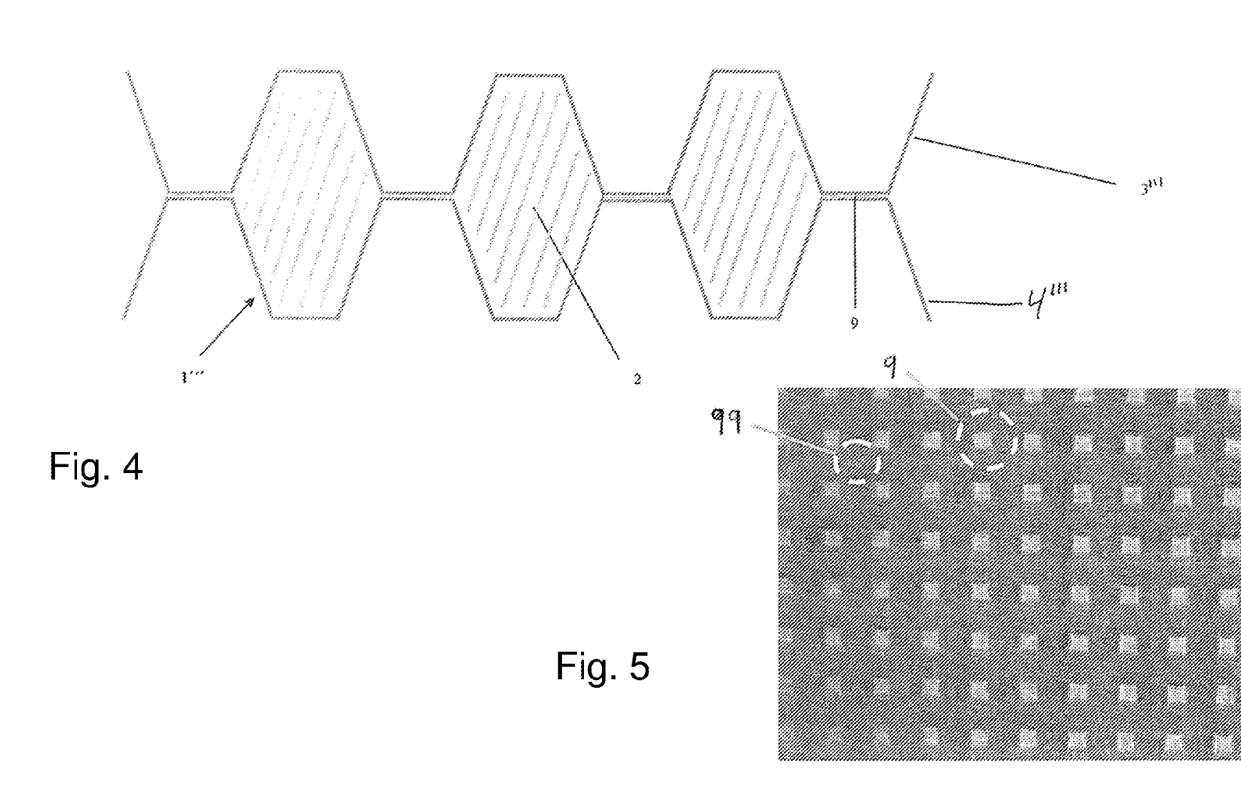
FIG. 4 shows a sheet with three layers and embossing from both sides.
FIG. 5 shows a photo of the sheet shown in FIG. 4.

FIG. 4 shows a fourth and preferred embodiment wherein the sheet 1''' is compressed in separately embossed areas 9 by patterned embossing with two calendar rollers during a production process of the product. The embossing with punctiform depressions 9 is provided from both outer layers 3''', 4''' of the sheet 1'''. A depression 9 appears at each side of the finished product, the depressions 9 appearing symmetrical as they are produced by pressing the two outer layers equally against each other by the embossing action.

FIG. 5 shows that the embossed areas 9 are square. Between these embossed areas there are areas 99 which are not compressed. The embossed areas constitute about 15% of the total area.

Figure 6:
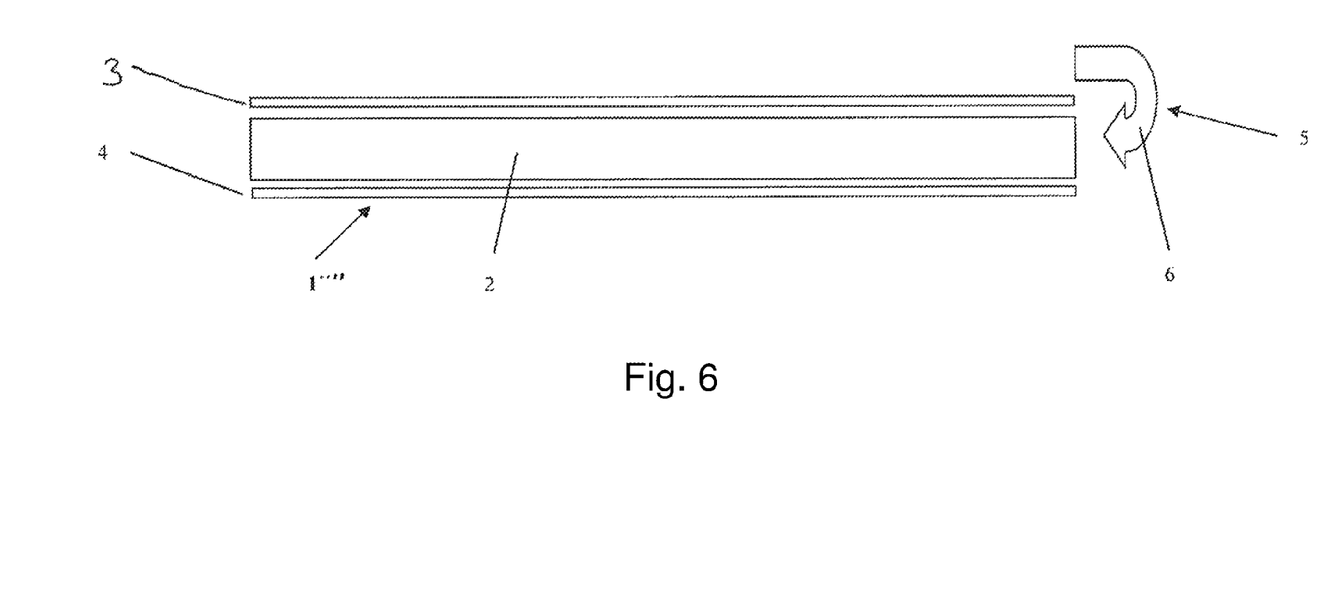
FIG. 6 shows a sheet with three layers and with the two outer layers as non-woven layers.

FIG. 6 shows a view corresponding to FIG. 1 but illustrating a fifth embodiment of a sheet 1'''' according to embodiments of the invention. The sheet 1 is made with a central layer 2 and a first outer layer 3 provided at one side of the central layer 2, and a second outer layer 4 at the opposite side of the central layer 2. The outer layers 3, 4 are made of non-woven layer or tissue allowing liquid to penetrate through to the central layer in which it is absorbed. In this embodiment, the liquid can furthermore flow out to the edge 5 of the sheet and then seep into the central layer from the edge of the sheet 1, as shown by arrow 6.

By the embodiments where the liquid can penetrate through the outer layer or layers, the edge of the sheet can be closed.

FIGS. 1, 2 and 6 illustrate the construction of the sheet, showing sectional views that do not go through the embossed areas. However, in the embodiments shown in FIGS. 1, 2 and 6 there will also appear embossings that establish attachment points as explained with reference to FIGS. 3-5.

Figure 7:
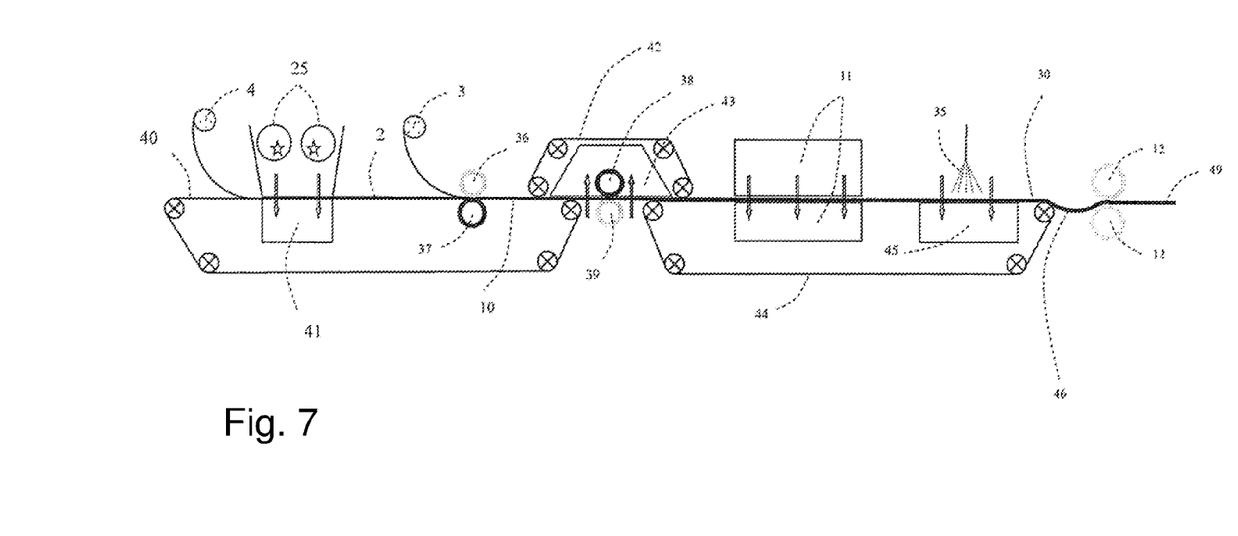
FIGS. 7-11 show various embodiments of a production process.

FIG. 7 shows schematically a production method of the sheet 1 occurring in long webs in a continuous process. A continuous airlaid central web 2 is made in a formerhead 25 interacting with a vacuum box 41 and forming the web 2 on a formerwire 40. The central web 2 includes a mixture of cellulosic fibres, superabsorbents and heat-adhesive binder fibres. Before the formerhead 25 there is supplied an outer web 4 on which the fibre web is formed. An outer web 3 is supplied on the top side of the central web 2 after the formerhead 25. The first 3 and second 4 continuous outer webs are of fibre, tissue or non-woven in order thereby to form a sandwich web 10 of the web with at least three layers 2, 3, 4.

The web 10 with the at least three layers is moved through a first compacting unit with a hot compacting roller 36 disposed over the web 10 and interacting with a counter-roller 37, and a second compacting unit wherein a second hot compacting roller 39 and the counterroller 38 are disposed such that the sandwich-web 10 is also impacted by the hot compacting roller 39 from below. The web 10 is transferred by a transfer unit with a transfer wire 42 acting with an upwardly directed vacuum 43 to an ovenwire 44.

The ovenwire 44 moves the web through a heating zone 11, such as a heated oven with circulating air, but which is not a heated calendar roller, for heating the web 10. The heating temperature and the heating time are adapted for at least a partial melting of the heat-adhesive binder fibres in the central layer in order to bind the fibres in the central layer 2 and for binding the outer layers 3, 4 to the central layer 2.

The dried web 10 is then subjected to moisturising in a moisturising unit 35 operating with vacuum 45.

The web is moved on, and now there is such a strength in the web that it is possible that the web 10 can appear with a freely suspended part 46 before being subjected to calendaring in a calendar unit with two calendar rollers 12 that emboss the web with punctiform or linear depressions from both sides of the web 10. The finished multi-layered web 49 then appears with embossings that establish attachment points.

The webs 3 and 4 are air-permeable and can be non-woven webs.

Alternatively, one calendar roller can be substituted by a following smooth calendar roller.

Cutting up of the web 49 into single sheets occurs typically in a subsequent process and is therefore not shown in connection with the web making.

Figure 8:
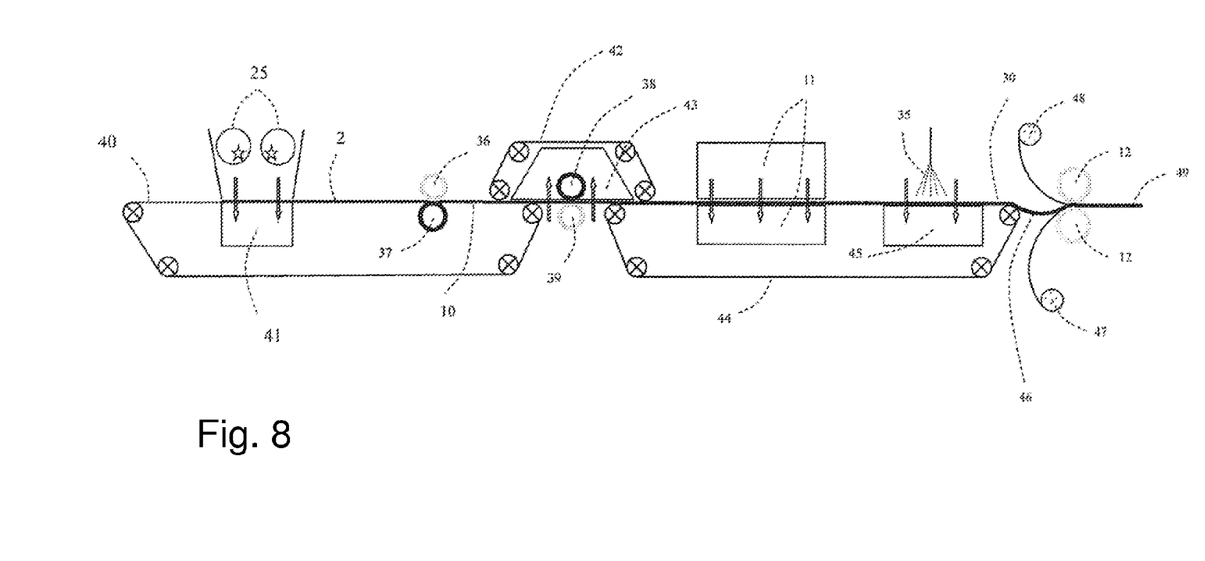

FIG. 8 shows schematically a production method of the sheet 1 occurring in long webs in a continuous process. A continuous airlaid central web 2 made in a formerhead 25 by an airlaid process of a mixture of cellulosic fibres, superabsorbents and heat-adhesive binder fibres is passed through a first and a second compacting unit and is transferred via a transferwire 42 to an ovenwire 44 moving the web through a heating zone 11, such as a heated oven with circulating air, but which is not a heated calendar roller, for heating the web, wherein the heating temperature and the heating time are adapted to at least partial melting of the heat-adhesive binder fibres in the central layer for activating the binder fibres in the central layer 2.

After the heating zone 11 the dried web 10 is subjected to moisturising in a moisturising unit 35 operating with vacuum 45.

The outer layers 47 and 48 are then unwound at each their side of the central layer 2. The multi-layered web 30 is then subjected to calendaring with a calendar roller 12 embossing the web with punctiform or linear depressions at both sides of the web 30 as the heated embossed calendar rollers 12 interact such that the finished multi-layered web 49 appear with symmetrical embossings that establish attachment points. Cutting up of the web 49 into single sheets occurs in a subsequent process and is therefore not shown in connection with making the multi-layered web.

The webs 47 and 48 can be permeable or impermeable. They may be films or non-woven or tissue webs.

Figure 9:
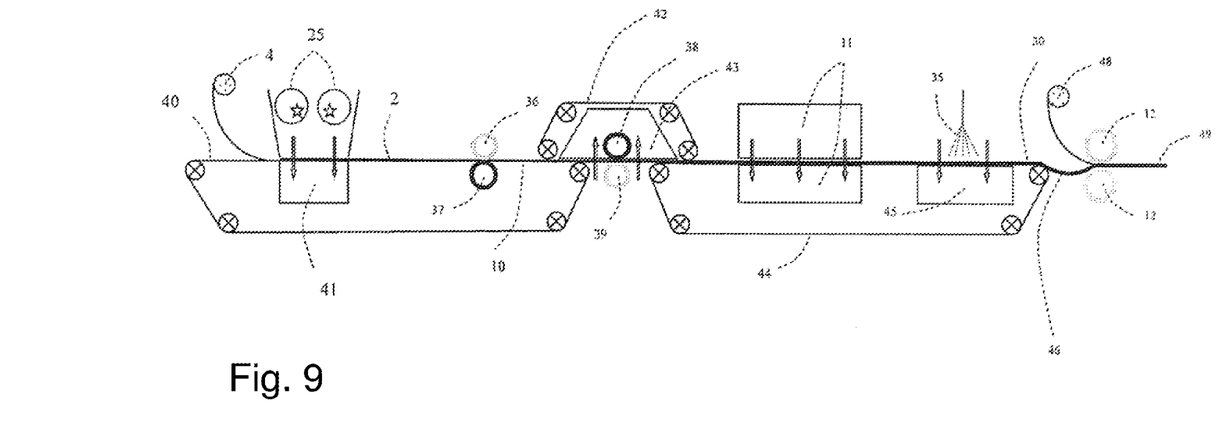

FIG. 9 shows schematically a production method for products according to embodiments of the invention occurring in long webs in a continuous process. A continuous airlaid central web 2 is made in an airlaid process of a mixture of cellulosic fibres, superabsorbents and heat-adhesive binder fibres and produced in a formerhead 25. Before the formerhead 25 there is supplied an outer web 4 on which the fibre web 2 is formed. After the formerhead 25 the web 2, 4 is passed through a first and a second compacting unit and transferred via a transferwire 42 to an ovenwire 44 moving the web through a heating zone 11, such as a heated oven, but which is not a heated calendar roller, for heating the web 10, wherein the heating temperature and the heating time are adapted to at least partial melting of the heat-adhesive binder fibres in the central layer for activating the binder fibres in the central layer 2.

After moisturising in the moisturising unit 35, an outer web 48 is supplied from one side of the central web 2. The web 30 is then subjected to calendaring with two calendar rollers 12 embossing the web with punctiform or linear depressions at both sides of the web 30 as the heated embossed calendar rollers 12 interact such that the finished multi-layered web 49 appear with symmetrical embossings that establish attachment points. Cutting up of the web 49 into single sheets occurs in a subsequent process and is therefore not shown in connection with making the multi-layered web.

The web 4 is air-permeable and a non-woven or tissue web. The web 48 can be permeable or impermeable. It may be a film or non-woven or tissue web.

Figure 10:
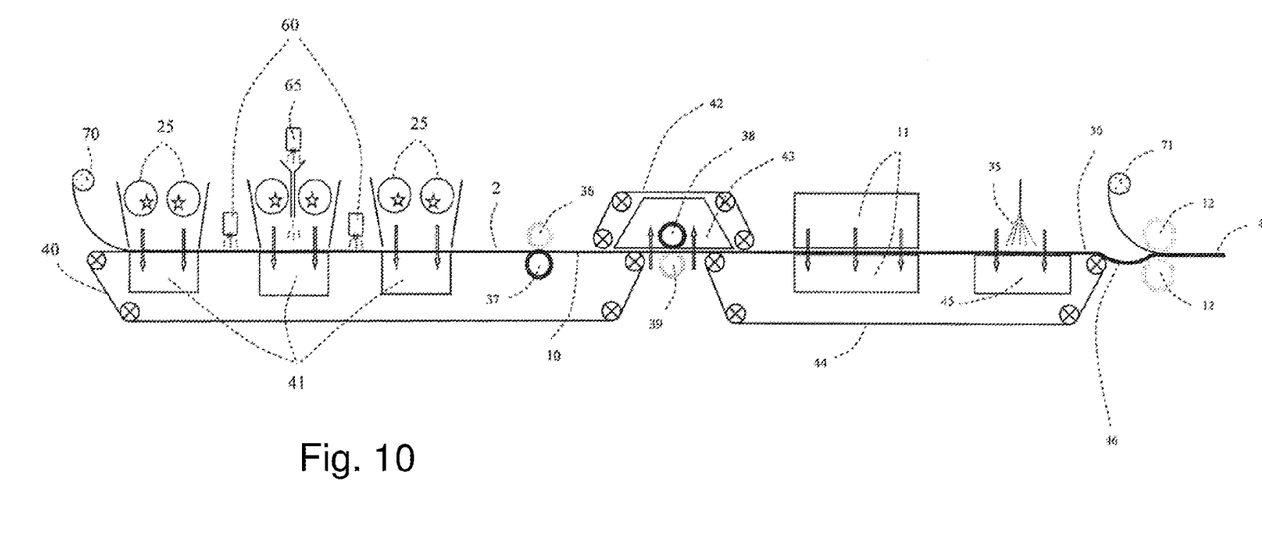

FIG. 10 shows schematically a production method for products according to embodiments of the invention occurring in long webs in a continuous process. A continuous airlaid central web 2 made in an airlaid process of a mixture of cellulosic fibres, superabsorbents and heat-adhesive binder fibres produced in three formerheads 25. Three formerheads are used in order for granulate from superabsorbent dispensers 60 and 65 to be distributed homogenously throughout the thickness of the web 2.

Before the formerhead 25 there is supplied an outer web 70 on which the fibre web 2 is formed. After the formerhead 25 the web 2,4 is passed through a first and a second compacting unit and transferred via a transferwire 42 to an ovenwire 44 moving the web through a heating zone 11.

After moisturising in the moisturising unit 35, an outer web 71 is supplied from one side of the central web 2. The web 30 is then subjected to calendaring with two calendar rollers 12 embossing the web with punctiform or linear depressions at both sides of the web 30.

The web 70 is air-permeable and can be a non-woven or tissue web. The web 71 can be permeable or impermeable. It may be a film or non-woven or tissue web.

Figure 11:
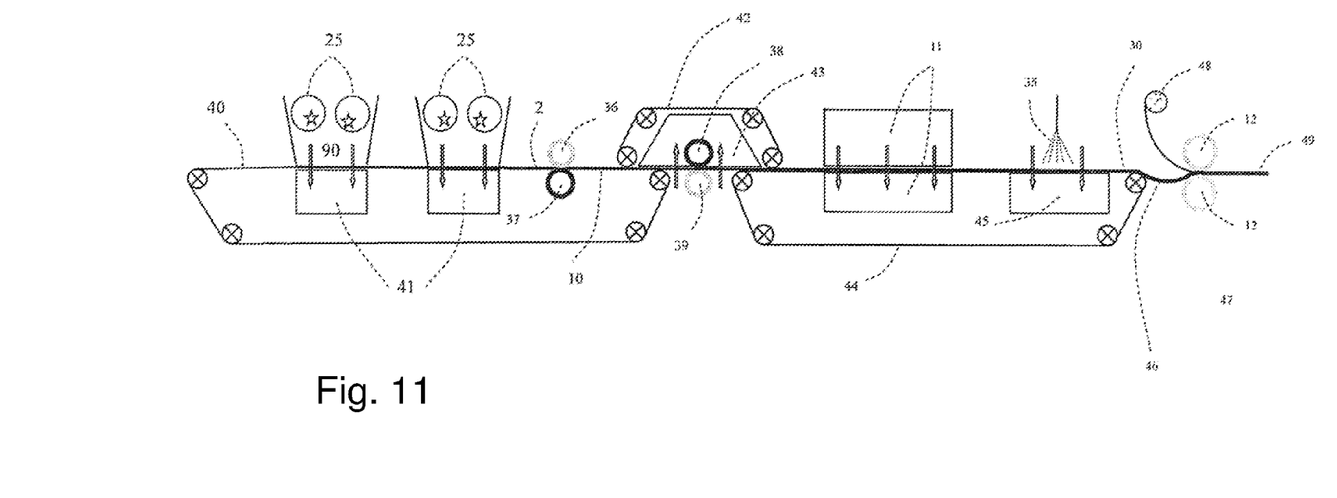

FIG. 11 shows schematically a production method for products according to embodiments of the invention occurring in long webs in a continuous process. A continuous airlaid central web 2 is made in an airlaid process of a mixture of cellulosic fibres, superabsorbents and heat-adhesive binder fibres and produced in a formerhead 25. In front of this formerhead 25 there is disposed a further formerhead 25 which is used for forming an outer layer 90 upon which the fibre web 2 is formed.

In the first formerhead is formed a web of 100% heat-adhesive binder fibres instead of first unwinding a previously formed web of non-woven or tissue.

After the formerheads 25 the web 2, 90 is passed through a first and a second compacting unit and transferred via a transferwire 42 to an ovenwire 44 moving the web through a heating zone 11, such as a heated oven, wherein the heating temperature and the heating time are adapted to at least partial melting of the heat-adhesive binder fibres in the outer layer 90 and the central layer 2 for activating the binder fibres.

After moisturising in the moisturising unit 35, an outer web 48 is supplied from one side of the central web 2.

The web 30 is then subjected to calendaring by two calendar rollers 12 embossing the web with punctiform or linear depressions at both sides of the web 30 as the heated embossed calendar rollers 12 interact such that the finished multi-layered web 49 appear with symmetrical embossings that establish the attachment points.

Cutting up of the web 49 into single sheets occurs in a subsequent process and is therefore not shown in connection with making the multi-layered web.

The web 48 can be permeable or impermeable. It may be a film or non-woven or tissue web.

Figure 12:
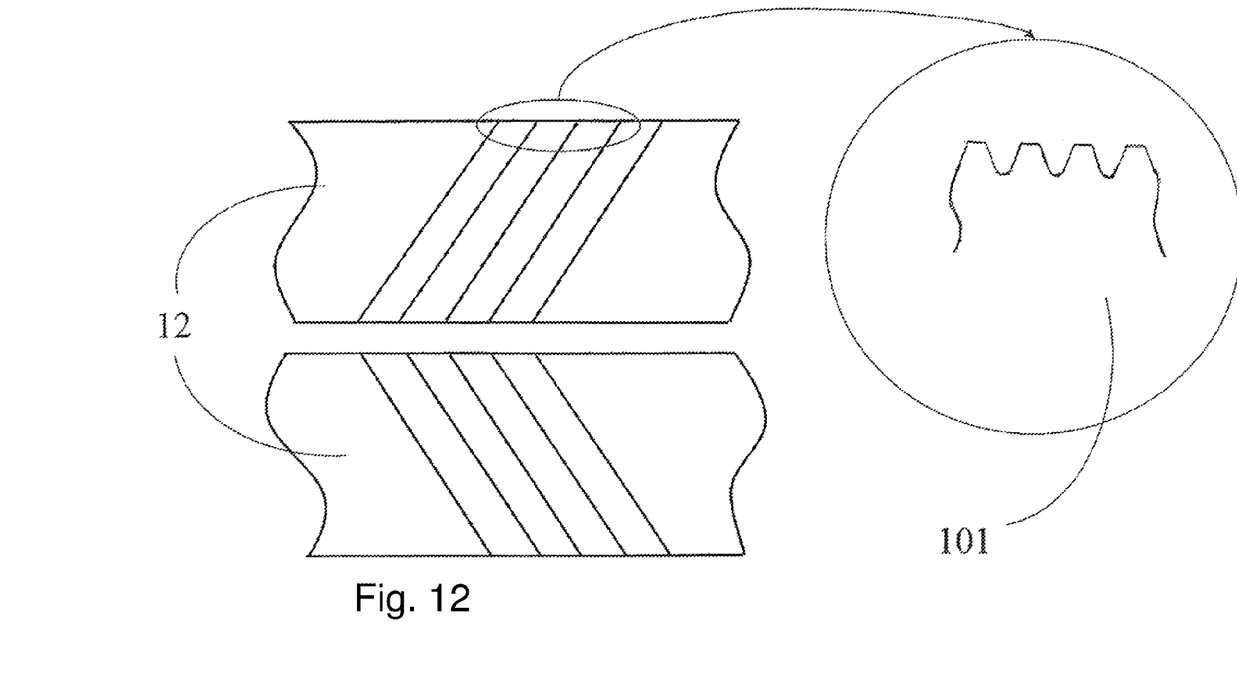
FIG. 12 shows a schematic view of two calendar rollers applied in a method.

FIG. 12 shows two calendar rollers applied in a method according to embodiments of the invention. The rollers 12 are provided with linear elevations 101 as seen on the enlarged view. These elevations 101 are formed on both calendar rollers 12 and run at 45° relative to the axial extension of the rollers. Since the elevations 101 have orientations that are oppositely (differently) directed, the attachment points will be formed where the linear elevations 101 intersect.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A product including a liquid-absorbing multi-layered sheet with a liquid-absorbing central layer and a first and a second outer layer of fibres, tissue or film provided at each their side of the central layer; wherein the central layer is airlaid and includes cellulosic fibres, superabsorbents and heat-adhesive binder fibres; wherein a percentage of heat-adhesive binder fibres in the central layer is between 1% and 7% of a total weight of fibres in the central layer, and wherein the central layer has a density less than 400 kg/m$^3$, wherein the multi-layered sheet has embossings that form separate areas which are compressed for establishing attachment points constituting between 10% and 20% of the area of the sheet.

2. The product according to claim 1, wherein the sheet has embossings in the form of distinct local depressions applied on either sides of the sheet.

3. The product according to claim 1, wherein the first and second outer layers are constituted by non-woven layers or tissue, or wherein the first outer layer is constituted by a non-woven layer or tissue and the second outer layer is constituted by a film.

4. The product according to claim 1, wherein the area of each of the attachment points is between 1.2 and 2.5 mm$^2$.

5. The product according to claim 1, wherein the attachment points are rectangular.

6. The product according to claim 1, wherein the first outer layer is constituted by a film or wherein both outer layers are constituted by film.

7. The product according to claim 1, wherein the sheet along the edges is a liquid-permeable structure through which liquid can be conducted from the edge and into the central layer.

8. The product according to claim 1, wherein the multi-layered sheet has embossings that form the separate areas which are compressed for establishing the attachment points constituting 15% of the area of the sheet.

9. The product according to claim 1, wherein the percentage of the heat adhesive fibres is between 1% and 5%.

10. A method for producing a multi-layered web for forming sheets according to claim 1, wherein there is produced a continuous airlaid central web of a mixture of cellulosic fibres, superabsorbents and heat-adhesive binder fibres with a density less than 400 kg/m$^3$;

wherein heat-adhesive binder fibres are supplied to the central layer, the binder fibres constituting between 1% and 7% of the total weight of fibres in the central layer;

wherein a first and a second continuous outer web of fibres, film or tissue is provided at each their side of the central web in order thereby to form a 3-layered structure of the web; wherein the heat-adhesive binder fibres are preferably added in a percentage between 1% and 5%, preferably between 2% and 4%, wherein the central layer is subjected to a compacting with heated compacting rollers;

wherein the web or webs that are made air-permeable are moved through a heating zone for heating the web or webs, respectively, wherein the heating temperature and the heating time is adapted to at least a partial melting of the heat-adhesive binder fibres in the central web in order to bind the fibres in the central web;

wherein the formed webs are moistened after the heating zone;

wherein webs that possibly are not air-permeable are unwound between the heating zone and a calendar unit which is operated with heated calendar rollers for hot calendaring, whereby the binder fibres are pressed into each other simultaneously with establishing hydrogen bindings between the cellulosic fibres;

wherein the central web is always subjected to heating prior to calendaring the jointed webs in the calendar unit, and wherein calendaring performs a patterned embossing with patterned rollers for embossing the surface of the multi-layered web with separate areas which are compressed for establishing attachment points that constitute between 10% and 20% of the area of the web.

11. The production method according to claim 10, wherein calendaring of the multi-layered web is performed by two interacting calendar rollers with embossing pattern in order thereby to provide embossing on both sides of the web.

12. The production method according to claim 10, wherein at least one of the calendaring rollers is provided on its surface with linear elevations in order thereby to form an embossing pattern in the surface of the multi-layered web.

13. The production method according to claim 12, wherein the linear elevations are formed on both calendar rollers extending at 45° relative to the axial extension of the rollers, wherein the orientation is oppositely directed such that the attachment points are formed where the linear elevations intersect each other.

14. The production method according to claim 10, wherein the multi-layered product is made such that the area of each of the attachment points is between 1.2 and 2.5 mm$^2$.

15. The production method according to claim 10, wherein the first and second outer layers are constituted by non-woven layers or tissue, or wherein one outer layer is constituted by a non-woven layer or tissue and the other outer layer is constituted by a film.

16. The use of a sheet according to claim 4 for absorbing liquid from meat juice from meat, and wherein the first outer layer is oriented towards the meat.

\* \* \* \* \*